United States Patent
Helaoui et al.

(10) Patent No.: US 11,105,792 B2
(45) Date of Patent: Aug. 31, 2021

(54) SYSTEM AND METHOD FOR DETECTING HALITOSIS

(71) Applicant: KONINKLIJKE PHILIPS N.V., Eindhoven (NL)

(72) Inventors: Rim Helaoui, Eindhoven (NL); Amir Hussein Rmaile, Eindhoven (NL); Radu Serban Jasinschi, Nuenen (NL); Ronaldus Maria Aarts, Geldrop (NL); Caifeng Shan, Veldhoven (NL); Jayprakash Patel, Wembley (GB); Marinus Karel Johannes De Jager, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 265 days.

(21) Appl. No.: 15/739,290

(22) PCT Filed: Jun. 24, 2016

(86) PCT No.: PCT/EP2016/064759
§ 371 (c)(1),
(2) Date: Dec. 22, 2017

(87) PCT Pub. No.: WO2016/207409
PCT Pub. Date: Dec. 29, 2016

(65) Prior Publication Data
US 2018/0180591 A1    Jun. 28, 2018

(30) Foreign Application Priority Data

Jun. 26, 2015 (EP) .................................... 15173968

(51) Int. Cl.
*G01N 33/497* (2006.01)
*A61B 1/24* (2006.01)
(Continued)

(52) U.S. Cl.
CPC ............. *G01N 33/497* (2013.01); *A61B 1/24* (2013.01); *A61B 5/004* (2013.01); *A61B 5/0077* (2013.01);
(Continued)

(58) Field of Classification Search
None
See application file for complete search history.

(56) References Cited

U.S. PATENT DOCUMENTS

| 4,823,803 A | 4/1989 | Nakamura |
| 7,064,830 B2 | 6/2006 | Giorgianni et al. |

(Continued)

FOREIGN PATENT DOCUMENTS

| JP | 2004194900 A | 7/2004 |
| JP | 2009205330 A * | 9/2009 |

(Continued)

OTHER PUBLICATIONS

Russell, Stuart, "Temporal probability models," 2005, UC Berkeley, Lecture Slides, Chapter 15a (Year: 2005).*

(Continued)

*Primary Examiner* — Etsub D Berhanu
*Assistant Examiner* — Aurelie H Tu (57) ABSTRACT

A system for detecting halitosis is disclosed that comprises a gas sensor (116) for generating a sensor signal signalling the detection of compounds indicative of halitosis exhaled through an oral cavity; an image sensor (114) for capturing an image (500, 510) of a dental condition and/or tongue condition in said oral cavity; and a processor (110) communicatively coupled to the gas sensor and the image sensor and adapted to process the sensor signal and the image in order to determine if in case of the sensor signal signalling the presence of a compound indicative of halitosis, said halitosis originates from said oral cavity by determining the (Continued)

dental condition and/or tongue condition in said image. A method for detecting halitosis and a computer program product implementing the method are also disclosed.

12 Claims, 4 Drawing Sheets

(51) Int. Cl.
*G06T 7/90* (2017.01)
*A61B 5/00* (2006.01)
*A61C 17/00* (2006.01)
*G06K 9/62* (2006.01)

(52) U.S. Cl.
CPC ............ *A61C 17/00* (2013.01); *G06K 9/6293* (2013.01); *G06T 7/90* (2017.01); *A61B 2560/0462* (2013.01); *A61B 2576/02* (2013.01); *G01N 2033/4975* (2013.01)

(56) References Cited

U.S. PATENT DOCUMENTS

| | | | | |
|---|---|---|---|---|
| 2006/0225744 | A1* | 10/2006 | Braunecker | G01N 33/497 128/897 |
| 2006/0281042 | A1* | 12/2006 | Rizoiu | A61C 17/22 433/29 |
| 2008/0183094 | A1* | 7/2008 | Schonfuss | A61B 5/097 600/532 |
| 2009/0317770 | A1 | 12/2009 | Gatzemeyer et al. | |
| 2010/0330000 | A1* | 12/2010 | Hellgren | A61K 9/0058 424/48 |
| 2011/0129939 | A1 | 6/2011 | Hsieh | |
| 2014/0134650 | A1* | 5/2014 | Hawtin | G01N 33/5011 435/7.92 |
| 2014/0194702 | A1 | 7/2014 | Tran | |
| 2015/0038350 | A1* | 2/2015 | Nishinaga | G01N 33/5302 506/9 |

FOREIGN PATENT DOCUMENTS

| | | |
|---|---|---|
| JP | 2009205330 | 9/2010 |
| JP | 2012147910 A | 8/2012 |
| JP | 20110008246 | 8/2012 |
| WO | 03/090704 A1 | 11/2003 |

OTHER PUBLICATIONS

Walsh: "On the Nose—New Diagnostic and Treatment Approaches for Oral Maladour"; Dental Practice, Jul./Aug. 2006, pp. 60-62.

Obrochta:"Efficient & Effective Use of Intraoral Camera"; dentalcare.com Continuing Education, Mar. 2011, 38 Page Document.

China Academic Journal Electronic Publishing House, pp. 481-485, 2004.

Xu et al: "Etiology and Treatment of Intra-Oral Halitosis"; Progress in Modern Biomedicine, vol. 11, No. 4, Feb. 2011, pp. 791-794.

Yasuda, et al, "Probabilistic graphical models: Bayesian networks and their surroundings", Operations Research, Japan, Japan Opera, Solutions Research Society, Apr. 2013, vol. 58, No. 4, p. 191-197— English Abstract.

* cited by examiner

SYSTEM AND METHOD FOR DETECTING HALITOSIS

CROSS-REFERENCE TO PRIOR APPLICATIONS

This application is the U.S. National Phase application under 35 U.S.C. § 371 of International Application No. PCT/EP2016/064,759 filed on Jun. 24, 2016, which claims the benefit of European Patent Application No. 15173968.7 filed on Jun. 26, 2015. These applications are hereby incorporated by reference herein.

FIELD OF THE INVENTION

The present invention relates to a system for detecting halitosis, comprising a gas sensor for generating a sensor signal signalling the detection of compounds indicative of halitosis exhaled through an oral cavity.

The present invention further relates to a method for detecting halitosis, comprising receiving a sensor signal signalling detection of compounds indicative of halitosis exhaled through an oral cavity from a gas sensor.

The present invention yet further relates to a computer program product comprising a computer-readable data carrier carrying computer program code for, when executed on the above system, causing a processor of the system to implement the above method.

BACKGROUND OF THE INVENTION

Halitosis is a condition referring to unpleasant odours in expired air. Halitosis may come from different sources, e.g. oral malodour originating from the oral cavity, which may be caused by poor oral hygiene, or systemic halitosis having pathological causes such as anaemia, cyanosis, diabetes, kidney diseases and so on.

Halitosis can be detected by analysing expelled air, as the unpleasant odours are typically caused by sulphur-containing gaseous or volatile compounds in the expelled air, such as dimethyl sulfide, hydrogen sulfide, dimethyl disulphide and methane thiol (methyl mercaptan). Such sulphur-containing gaseous or volatile compounds for instance may be detected by artificial olfactory systems including compact gas sensors such as electronic noses (e-noses). An example of such an artificial olfactory system is disclosed in US 2014/0096590 A1.

Due to the social impact of halitosis, halitosis sufferers typically want to alleviate the symptoms of halitosis, and preferably eradicate the root cause of the halitosis where possible, e.g. in the case of oral malodour caused by poor oral hygiene. This therefore requires a determination of this root cause. At present, this is typically done by dentists or oral hygienists, e.g. by periodontal evaluation and plaque scoring. This is not ideal, as a halitosis sufferer only visits such professional infrequently, e.g. once or twice annually, and this does not facilitate feedback on the measures put into place to tackle the oral malodour, e.g. changes in oral hygiene regimes such as dental hygiene, e.g. brushing teeth, inter-dental cavity cleaning, tongue cleaning, and so on, to monitor if the recommended oral hygiene techniques to tackle oral cavity originating halitosis are applied correctly. There exists a need for an automated system and method that can assist its user to tackle oral malodour more effectively.

JP2012147910 A discloses an oral cavity observing device comprising an inserting part inserted in the oral cavity; a light-emitting part arranged in the inserting part and configured for emitting the irradiation light to the oral cavity; an imaging part configured for capturing an image of return light of the irradiation light emitted from the light-emitting part to the oral cavity; one or more biological information sensors configured for detecting biological information in the oral cavity; and a light-emitting regulating part configured for allowing to emit the irradiation light from the light-emitting part only when the biological information in the oral cavity is detected by the biological information sensors.

SUMMARY OF THE INVENTION

The present invention seeks to provide a system for improved detection of the source of halitosis in a person.

The present invention further seeks to provide a method for improved detection of the source of halitosis in a person.

The present invention yet further seeks to provide a computer program product implementing the method for improved detection of the source of halitosis in a person when executed on a system processor.

According to an aspect, there is provided a halitosis detecting system, comprising a gas sensor for generating a sensor signal signalling the detection of compounds indicative of halitosis exhaled through an oral cavity; an image sensor for capturing an image of a dental condition and/or tongue condition in said oral cavity; and a processor communicatively coupled to the gas sensor and the image sensor and adapted to process the sensor signal and the image in order to determine if in case of the sensor signal signalling the presence of a compound indicative of halitosis, said halitosis originates from said oral cavity by determining the dental condition and/or tongue condition in said image.

The invention is based on the insight that upon detecting one or more compounds indicative of halitosis with a gas sensor such as an electric nose (e-nose), image information of the oral cavity through which the one or more compounds are exhaled can be evaluated to determine a condition of an object in the oral cavity, i.e. dental condition and/or tongue condition to determine a likelihood of the halitosis compounds originating from the oral cavity, i.e. being caused by the dental and/or tongue condition and to provide feedback on whether the oral cavity is properly cleaned to improve, i.e. reduce, the halitosis. The processor may be adapted to implement a probabilistic model using the determined dental condition and/or tongue condition in order to determine if the halitosis originates from said oral cavity. This for instance has the advantage that variations in detected concentrations of the one or more compounds indicative of halitosis and/or variations in the dental condition and/or tongue condition can be taken into account by the processor to generate an indication of the likelihood of the source of the halitosis, e.g. by assigning a confidence score to the determined source based on the observed concentrations of the one or more compounds indicative of halitosis and/or variations in the dental condition and/or tongue condition.

The probabilistic model preferably is a temporal probabilistic model, wherein the processor may be adapted to determine if the halitosis originates from said oral cavity based on a series of determined dental conditions and/or tongue conditions determined at different points in time. This can improve the accuracy of the determination of the source of the halitosis as well as provide more accurate feedback on the effectiveness of the oral hygiene techniques.

The processor may be adapted to apply a colour normalization algorithm to the image in order to normalize tongue colour prior to processing the normalized image. This facilitates capturing images with different devices or under different lighting conditions, as the differences between images resulting from the use of different devices or image capturing under different lighting conditions are removed by the normalization.

The processor may be adapted to determine if in case of the sensor signal signalling the presence of a compound indicative of halitosis, said halitosis originates from said oral cavity by determining the dental condition and/or tongue condition in said image in combination with evaluating personal data provided by a user of the system. This may further improve the accuracy of the halitosis source determination.

In an embodiment, the gas sensor, the image sensor and the processor are integrated in a single device.

In an alternative embodiment, the system comprises a first device including the processor and the image sensor, the first device further comprising a wireless communication module communicatively coupled to the processor and a second device including the gas sensor and a further wireless communication module for communicating with the wireless communication module.

The second device advantageously may comprise an electronic oral hygiene device to facilitate halitosis compound detection during brushing the teeth of a person, thus obviating the need for a separate action to perform this detection.

The single device or the first device may be a head-mountable device.

The system may further comprise a display device communicatively coupled to the processor, wherein the processor is adapted to control the display device to display oral hygiene instructions on the display device in response to the halitosis determination. In this manner, a user of the system can be guided in a particularly effective manner to improve the dental and/or tongue condition in the oral cavity and reduce or even eradicate halitosis from the oral cavity.

According to another aspect, there is provided a method for detecting halitosis, comprising receiving a sensor signal signalling detection of compounds indicative of halitosis exhaled through an oral cavity from a gas sensor; receiving an image of a dental condition and/or tongue condition in said oral cavity from an image sensor; and processing the sensor signal and the image in order to determine if in case of the sensor signal signalling the presence of a compound indicative of halitosis, said halitosis originates from said oral cavity by determining the dental condition and/or tongue condition in said image. Such a method facilitates improved halitosis source detection and monitoring by combining the gas sensor data and the image sensor data of the oral cavity.

The steps of receiving a sensor signal signalling detection of compounds indicative of halitosis exhaled through an oral cavity from a gas sensor; receiving an image of a dental condition and/or tongue condition in said oral cavity from an image sensor; and processing the sensor signal and the image in order to determine if in case of the sensor signal signalling the presence of a compound indicative of halitosis, said halitosis originates from said oral cavity by determining the dental condition and/or tongue condition in said image may be performed prior to cleaning the oral cavity and repeated after cleaning the oral cavity such that the method can verify the origin of the halitosis as determined prior to cleaning the oral cavity with the origin of the halitosis as determined after cleaning the oral cavity. This improves the accuracy of the halitosis source determination.

The method may further comprise applying a probabilistic model using the determined dental condition and/or tongue condition in order to determine if the halitosis originates from said oral cavity.

The probabilistic model may be a temporal probabilistic model, the method further comprising determining if the halitosis originates from said oral cavity based on a series of determined dental conditions and/or tongue conditions determined at different points in time.

In a preferred embodiment, the method further comprises applying a colour normalization algorithm to the image in order to normalize tongue colour prior to processing the image such as to cancel out differences in image characteristics that are the result from taking the images with different devices and/or under different lighting conditions.

According to yet another aspect, there is provided a computer program product comprising a computer-readable data carrier carrying computer program code for, when executed on the system according to any of the above embodiments, causing the processor of said system to implement the method of any of the above embodiments. Such a computer program product facilitates improved halitosis source detection and monitoring by combining the gas sensor data and the image sensor data of the oral cavity.

BRIEF DESCRIPTION OF THE DRAWINGS

Embodiments of the invention are described in more detail and by way of non-limiting examples with reference to the accompanying drawings, wherein FIG. 1 schematically depicts a system according to an embodiment.

DETAILED DESCRIPTION OF THE EMBODIMENTS

It should be understood that the Figures are merely schematic and are not drawn to scale. It should also be understood that the same reference numerals are used throughout the Figures to indicate the same or similar parts.

In the context of the present application, a head-mountable computing device is a device that can be worn of the head of its user and provides the user with computing functionality. The head-mountable computing device may be configured to perform specific computing tasks as specified in a software application (app) that may be retrieved from the Internet or another computer-readable medium. Non-limiting examples of such head-mountable computing devices include smart headgear, e.g. eyeglasses, goggles, a helmet, a hat, a visor, a headband, or any other device that can be supported on or from the wearer's head, and so on.

In the context of the present application, a portable computing device such as a head-mountable computing device comprises an image sensor for capturing an image of the oral cavity of its wearer. The image sensor may be arranged such that when the portable computing device is used as intended, the image sensor is oriented such that it can directly capture the image of the oral cavity, or is oriented such that it can capture a mirror image of the oral cavity in a mirror when its wearer is facing the mirror. Any suitable image capturing device may be used as image sensor, e.g. a camera.

Such an image sensor may be integral to the portable computing device, such as integrated in a lens of a head-mountable computing device through which its wearer observes its field of view, in a lens holder or frame for such a lens, or in any other suitable structure of the portable computing device in which the image sensor aligns with the field of view of the wearer of the head-mountable computing device, e.g. such that the image sensor is directed at the oral cavity when its wearer looks at the oral cavity in a mirror. Alternatively, the image sensor may be physically separated from the portable computing device, for instance may be a hand-held image sensor communicatively coupled to the portable computing device via a wired or a wireless connection. The image sensor may be part of a modular computing device, e.g. a head-mounted image sensor module communicatively coupled via a wired or wireless connection to one or more other modules of the modular computing device, wherein at least some of the other modules may be worn on parts of the body other than the head, or wherein some of the other modules may not be wearable, but portable instead for instance.

In the context of the present application, a gas sensor means any sensor capable of providing an artificial olfactory sensor, such as an electronic nose. The gas sensor may form an integral part of a portable computing device such as a head-mountable computing device also including the image sensor or may be physically separated from the portable computing device including the image sensor, for instance may be a part of a hand-held device communicatively coupled to the image sensor-containing computing device via a wired or a wireless connection. The gas sensor may be part of a modular wearable computing device, e.g. a head-mounted or hand-held gas sensor containing device communicatively coupled via a wired or wireless connection to one or more other modules.

Figure 1:
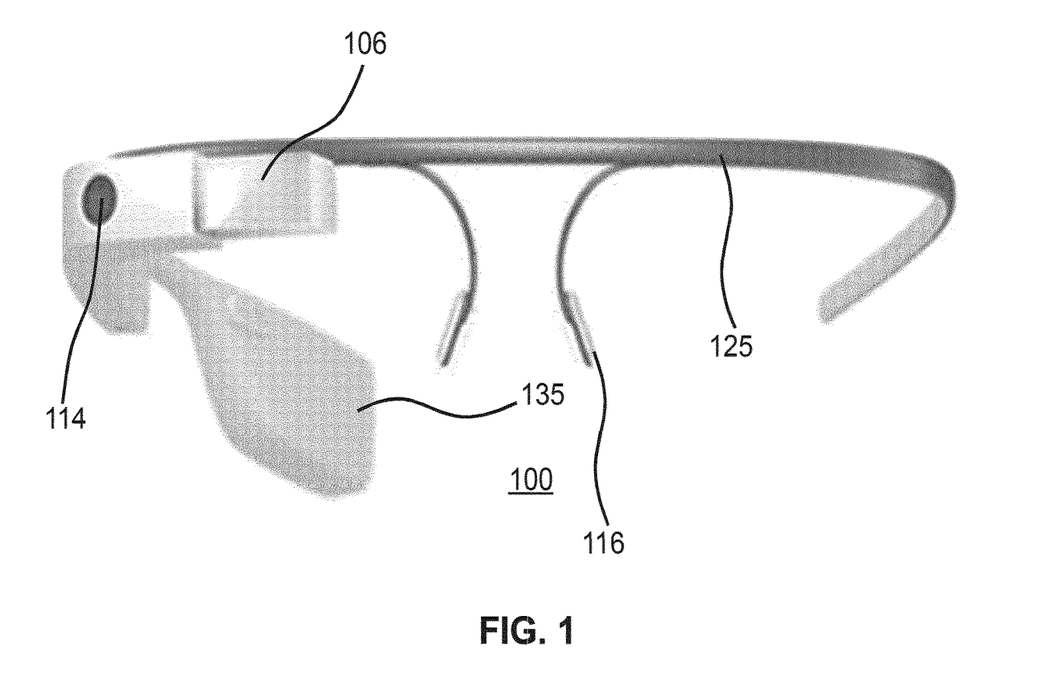
Figure 2:
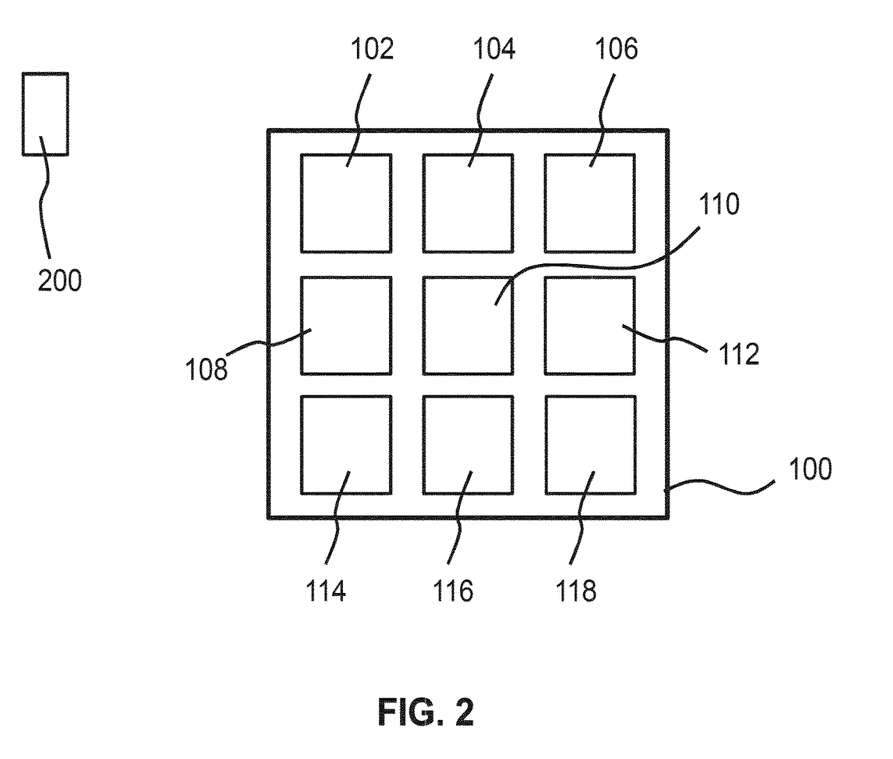
FIG. 2 schematically depicts an aspect of the system of FIG. 1.

FIG. 1 schematically depicts an embodiment of a system for detecting halitosis, here in the form of a head-mountable computing device 100. FIG. 2 schematically depicts a block diagram of an embodiment of the head-mountable computing device 100, further highlighting the functionality of the head-mountable computing device 100 in terms of functional blocks, at least some of which may be optional functionality. By way of non-limiting example, the head mountable computing device 100 is depicted as smart glasses, but it should be understood that the head-mountable computing device 100 may take any suitable shape as previously explained.

The head-mountable computing device 100 comprises an image sensor 114 for capturing an image of the oral cavity of the wearer and a gas sensor 116 for determining the presence of compounds indicative of halitosis in breath exhaled by the wearer of the head-mountable computing device 100. Any suitable image sensor 114 and gas sensor 116 may be integrated in the head-mountable computing device 100 for this purpose.

The head-mountable computing device 100 may comprise at least one transparent or see-through display module 106, under control of a discrete display controller (not shown). Alternatively, the display controller may be implemented by a processor 110 of the head-mountable computing device 100, as shown in FIG. 2.

When present, the at least one display module 106 is typically arranged to cover the field of view of the wearer when the head-mountable computing device 100 is worn by the wearer such that a wearer of the head-mountable computing device 100 may observe the field of view through an image displayed on the at least one the display module 106. In an embodiment, the head-mountable computing device 100 comprises a pair of transparent display modules 106 including a first display module that can be observed by the right eye of the wearer and a second display module that can be observed by the left eye of the wearer. Alternatively, the at least one display module 106 may be a single display module covering both eyes of the wearer.

The at least one display module 106 may be provided in any suitable form, such as a transparent lens portion as shown in FIG. 1 onto which an image is projected as is well-known per se. Alternatively, the head-mountable computing device 100 may comprise a pair of such a lens portions, i.e. one for each eye as explained above. The one or more transparent lens portions are dimensioned such that substantially the entire field of view of the wearer is obtained through the one or more transparent lens portions. For instance, the at least one display module 106 may be shaped as a lens to be mounted in the frame 125 or component housing 135 of the head-mountable computing device 100.

It will be understood that the frame 125 may have any suitable shape and may be made of any suitable material, e.g. a metal, metal alloy, plastics material or combination thereof. Several components of the head-mountable computing device 100 may be mounted in the frame 125, such as in a component housing 135 forming part of the frame 125. The component housing 135 may have any suitable shape, preferably an ergonomic shape that allows the head-mountable device 100 to be worn by its wearer in a comfortable manner.

The functioning of at least part of the head-mountable computing device 100 may be controlled by a processor 110 that executes instructions, i.e. computer program code, stored in a non-transitory computer readable medium, such as data storage 112. Thus, processor 110 in combination with processor-readable instructions stored in data storage 112 may function as a controller of the head-mountable computing device 100. In addition to instructions that may be executed by processor 110, data storage 112 may store data that is associated with the generation of semi-transparent images on the at least one display module 106.

In an embodiment, the head-mountable computing device 100 may be adapted to wirelessly communicate with a remote system, e.g. a further system 200 as shown in FIG. 2. To this end, the head-mountable computing device 100 may include a wireless communication interface 102 for wirelessly communicating with a remote target such as the remote further system 200. Any suitable wireless communication protocol may be used for any of the wireless communication between the head-mountable computing device 100 and the remote system 200, e.g., an infrared link, Zigbee, Bluetooth, a wireless local area network protocol such as in accordance with the IEEE 802.11 standards, a 2G, 3G or 4G telecommunication protocol, and so on. The remote further system 200 may for instance be controlled to provide the wearer of the head-mountable computing device 100 with feedback information and/or oral hygiene instructions, as will be further explained below.

The head-mountable computing device 100 may optionally comprise a further wireless communication interface 104 for wirelessly communicating with a further remote system, e.g. a wireless LAN, through which the head-mountable computing device 100 may access a remote data source such as the Internet, for instance to store data such as user preferences, user specific information, and so on. Alternatively, the head-mountable computing device 100 may include one wireless communication interface that is able to communicate with the remote further system 200 and a further remote target such as the further network. The processor 110 may further be adapted to control wireless communication interface 102 and, if present, wireless communication interface 104.

In an embodiment, the head-mountable computing device 100 may be arranged to detect a user instruction and to trigger an operation in response to the detected user instruction, e.g. using at least one further sensor 118 including a motion sensor like a gyroscope or similar in case the user instruction is a head motion, or by using the image sensor 114 or a camera to capture an image of a gesture-based instruction made by the wearer. Other suitable sensors for such gesture or motion capturing will be apparent to the skilled person. The processor 110 may be arranged to recognize a gesture or motion made by its wearer from the captured sensor data and to interpret the recognized gesture or motion as an instruction, for instance to identify a task performed by the wearer of the head-mountable computing device 100, e.g., reading, computing, and so on. Non-limiting examples of such a motion for instance include a turn or nod of the wearer's head. Non-limiting examples of such a gesture for instance include a hand or finger gesture in the field of view through the head-mountable computing device 100, which may be detected in an image captured with the image sensor 114.

Alternatively or additionally, the at least one further sensor 118 may include a sound sensor, e.g. a microphone, may be present to detect a spoken instruction, wherein the processor 110 may be communicatively coupled to the further sensor in order to process the sensor data and detect the spoken instruction.

The at least one further sensor 118 may additionally or alternatively include an input sensor, e.g. a button or the like for facilitating the wearer of the head-mountable computing device 100 to select the user instruction from a list of options. Such list of options for instance may be displayed on the at least one transparent display module 106 of the head-mountable computing device 100, when present.

The head-mountable computing device 100 may further include a user interface 108 for receiving input from the user. User interface 108 may include, for example, a touchpad, a keypad, buttons, a microphone, and/or other input devices. The processor 110 may control at least some of the functioning of head-mountable computing device 100 based on input received through user interface 108. In some embodiments, the at least one further sensor 118 may define or form part of the user interface 108.

Although FIG. 2 shows various components of head-mountable computing device 100, i.e., wireless communication interfaces 102 and 104, processor 110, data storage 112, image sensor 114, gas sensor 116 and the one or more further sensors 118, as being separate from the at least one display module 106, one or more of these components may be mounted on or integrated into the at least one display module 106. For example, an image capturing sensor may be mounted on a see-through display module 106, user interface 108 could be provided as a touchpad on a see-through display module 106, processor 110 and data storage 112 may make up a computing system in a see-through display module 106, and the other components of head-mountable computing device 100 could be similarly integrated into a see-through display module 106.

Alternatively, the head-mountable computing device 100 may be provided in the form of separate devices that can be worn on any part of the body or carried by the wearer, apart from at least the one display module 106, which typically will be mounted on the head. The separate devices that make up head-mountable computing device 100 may be communicatively coupled together in either a wired or wireless fashion.

In operation, the gas sensor 116 provides sensor readings to the processor 110, from which the processor 110 derives if halitosis has been detected in the exhaled breath analyzed by the gas sensor 116. The processor 110 for instance may be adapted to process raw sensor signals provided by the gas sensor 116 in order to determine the presence of volatile compounds in the exhaled breath indicative of halitosis, which may include the determination of a level of the volatile compounds in the exhaled breath, wherein halitosis is confirmed if the volatile compounds are present at a level exceeding a defined threshold. Alternatively, at least some of the processing of the raw sensor signals may be performed by the gas sensor 116, such that the processor 110 is provided with (pre-)processed sensor signals, e.g. signals in which levels of target volatile compounds have already been determined, such that the processor 110 may be configured to compare the determined levels of the target volatile compounds against a defined threshold in order to determine halitosis from the exhaled breath.

Upon the detection of halitosis, an image of the oral cavity is taken with the image sensor 114. This image should include at least one of the fronts of the teeth, possibly including part of the gums and an upper surface portion of the tongue. In order to achieve this, the wearer of the head-mountable computing device 100 may be prompted to have this image captured, e.g. by displaying an appropriate message on the display module 106, by producing an audible or tactile message and so on to trigger the wearer to open his or her mouth such that the image can be captured. For example, the wearer may be prompted to open his or her mouth and look at the open mouth in a mirror, such that an image sensor 114 aligned with a field of view of the wearer will capture a mirror image of the oral cavity in the mirror.

The captured image is subsequently processed by the processor 110 to determine if the detected halitosis is oral malodour. This may be done in a number of ways. For example, the image may be analyzed for clinical signs and symptoms indicating poor oral hygiene. This analysis may include at least one of the identification of food impacted within the interdental spaces between teeth, tongue coating, different stages of biofilm accumulation on the teeth surface, and certain periodontal conditions. The analysis may be implemented using suitable algorithms, e.g. objection recognition algorithms, colour evaluation algorithms, and so on. For example, a color feature vector may be extracted from the image based on the color ratios of the tongue gamut; dental plaques may be detected based on the yellowness of the teeth; certain periodontal diseases may be identified through the gum's apparent swelling and its reddishness and so on. The determined colour shading or grading may be categorized using a classification system in which each shade or grade is associated with a particular condition of the oral cavity, e.g. a simple three-category classification system (healthy, at risk, unhealthy) or a more refined or complex categorization system.

Based on the recognized objects and their color and/or shades or grades of colour, the hygienic condition of the oral cavity can be assessed, and a probability score of the likelihood of the halitosis originating from the oral cavity can be determined. If the probability score exceeds a defined threshold, the wearer of the head-mountable computing device 100 will be informed accordingly, and optionally presented with oral cavity cleaning instructions based on the image analysis, e.g. by providing cleaning instructions for the part(s) of the oral cavity having non-ideal cleanliness. Such cleaning instructions may be provided on the display module 106 or may be communicated by the wireless communication module 102 or 104 to a remote system 200 for display on the remote system, e.g. a smart mirror that the wearer of the head-mountable computing device 100 is facing. These are just some non-limiting examples of how this information may be presented to the wearer; many other examples will be immediately apparent to the skilled person.

In an embodiment, the head-mountable computing device 100 may be configured to repeat the above described halitosis assessment upon the wearer of the head-mountable computing device 100 performing oral cavity cleaning actions, e.g. brushing teeth, cleaning inter-dental cavities through flossing, inter-dental brushing and so on, tongue cleaning, e.g. scrubbing or brushing, and so on. The wearer may signal the head-mountable computing device 100 that oral cleaning has been completed, e.g. using a non-contact instruction, e.g. a gesture or the like or by contacting the user interface of the head-mountable computing device 100 to trigger the reassessment, i.e. to repeat the analysis of the exhaled breath and capturing and analysis of an image of the oral cavity if necessary to verify if the original determination of the origin of the halitosis was correct. In this manner, the original determination of the source of the halitosis may be reinforced or rectified.

Figure 3:
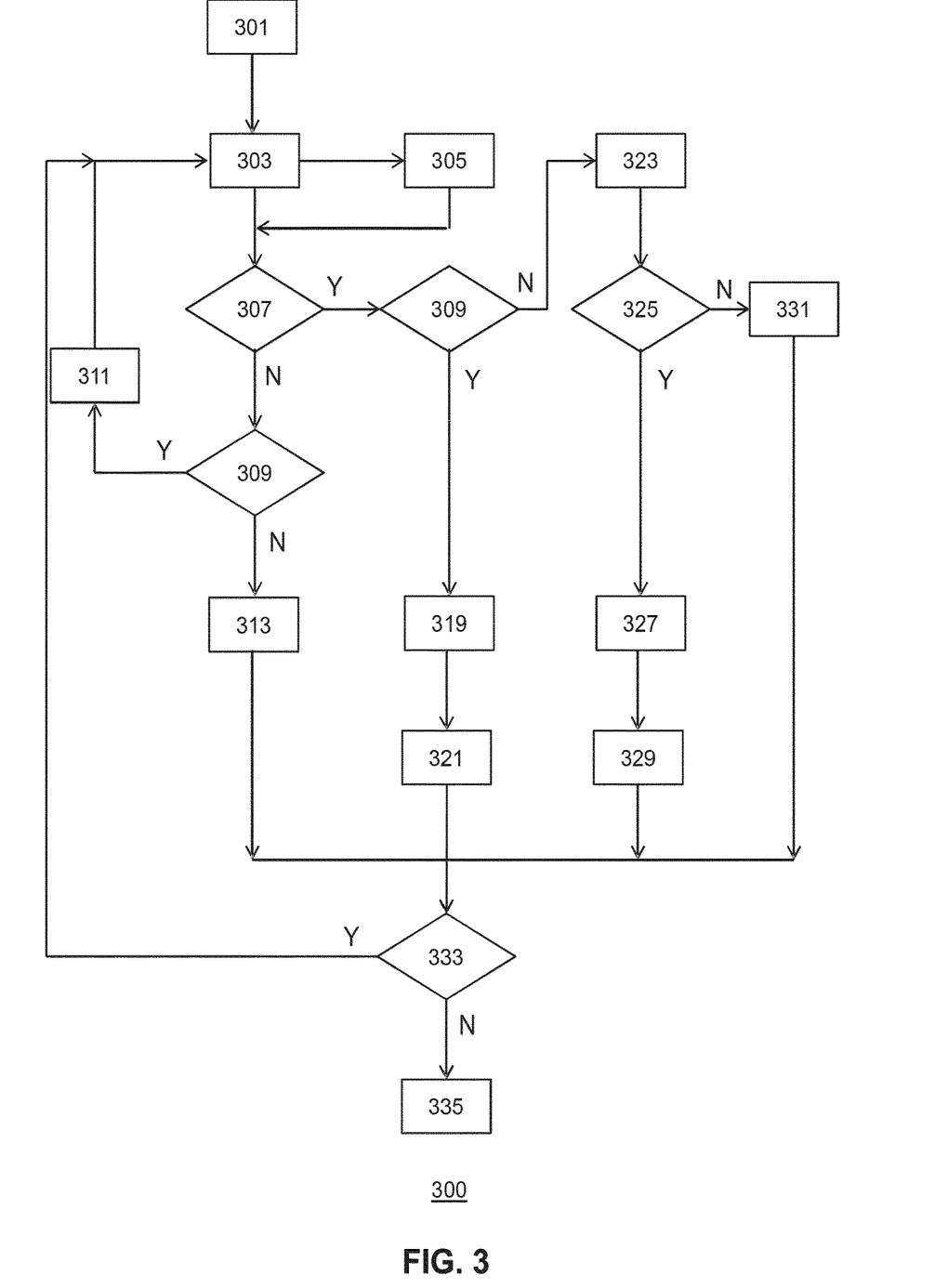
FIG. 3 is a flow chart of a method according to an embodiment.

The processor 110 may implement a method 300 for detecting halitosis as depicted in the flow chart of FIG. 3. The method 300 commences in step 301, e.g. by activating a halitosis detection operation of the head-mountable computing device 100, after which the method 300 progresses to step 303 in which exhaled breath is analyzed with the gas sensor 116. In step 305, an image is captured of the oral cavity with the image sensor 114, after which the sensor readings of the gas sensor 116 are interpreted to determine if halitosis is detected from the exhaled breath in step 307 and the hygiene levels in the oral cavity are checked in step 309 by evaluation of the captured image, e.g. by checking the oral cavity is sufficiently clean.

In case no malodour is detected in the exhaled breath as determined in step 307 but the oral cavity is not clean enough as determined in step 309, the method 300 proceeds to step 311 in which the wearer of the head-mountable computing device 100 is presented with the appropriate feedback, which may include cleaning instructions to improve the cleanliness of the oral cavity, after which the method 300 may return to step 303 to check if the provided feedback has led to an improvement in the condition of the oral cavity.

In case no malodour is detected in the exhaled breath as determined in step 307 and the oral cavity is clean enough as determined in step 309, the method 300 proceeds to step 313 in which the wearer of the head-mountable computing device 100 is provided with positive feedback, e.g. to maintain current cleaning regime for the cleaning of the oral cavity.

In case malodour is detected in the exhaled breath as determined in step 307 and the oral cavity is not clean enough as determined in step 309, the method 300 proceeds to step 319 in which oral hygiene as the source of halitosis is confirmed, e.g. by providing the wearer of the head-mountable computing device 100 with this determination, after which the method 300 proceeds to step 321 in which a treatment regime may be proposed to the wearer, which may include cleaning instructions to improve the cleanliness of the oral cavity.

In case malodour is detected in the exhaled breath as determined in step 307 but the oral cavity is clean enough as determined in step 309, the method 300 proceeds to step 323 in which the wearer of the head-mountable computing device 100 is prompted to answer one or more questions, e.g. yes/no questions, regarding the wearer exhibiting certain symptoms indicative of xerostomia, such as "altered taste?", "burning tongue?", and so on, as xerostomia can cause oral malodour in the absence of poor oral hygiene.

In step 325, the answered questions are evaluated to determine if the wearer of the head-mountable computing device 100 is likely to suffer from xerostomia. If this is the case, the method 300 proceeds to step 327 in which pseudo-halitosis, i.e. halitosis originating from the oral cavity but not caused by poor oral hygiene, is confirmed, e.g. by informing the wearer accordingly, followed by step 329 in which the wearer is provided with feedback regarding the likely causes of the halitosis, such as stress or medication, both of which are known triggers of xerostomia.

If on the other hand it is determined in step 325 that the detected halitosis is unlikely to be caused by xerostomia, the method 300 proceeds to step 331 in which the wearer of the head-mountable computing device 100 is informed about probable pathologies causing the halitosis, which may include a recommendation to seek professional medical assistance for a diagnosis of the cause of the halitosis.

It may be determined in step 333 if the halitosis evaluation should be repeated, for instance after the wearer of the head-mountable computing device 100 performing corrective actions such as oral cavity cleaning. If this is the case, the method 300 reverts back to step 303, else the method 300 terminates in step 335.

In the above method 300, where feedback is provided to the wearer of the head-mountable computing device 100, such feedback may be provided in any suitable form, for instance in textual form and/or in pictorial form, for instance using icons, cartoon characters, avatars, and so on to increase the engagement of the wearer of the head-mountable computing device 100. For example, tooth avatars may be generated that indicate the cleanliness of the oral cavity and/or the breath quality of the wearer.

It should be understood that the embodiment of the method 300 as shown in the flowchart of FIG. 3 is a non-limiting example of this embodiment, and that many alterations of this method may be made without departing from the present invention. For example, the image capturing step 305 may be performed prior to the exhaled breath evaluation step 303 or may be performed conditionally, i.e. only if it is determined in the exhaled breath that volatile compounds indicative of halitosis are present. Similarly, at least some of the feedback steps may be omitted. Other modifications will be apparent to the skilled person.

In a particularly suitable embodiment, the processor 110 may be arranged to perform the halitosis evaluation using a probabilistic model, which may include user-specific parameters to further increase the accuracy of the halitosis evaluation. This is explained in further detail with the aid of FIG. 4, which schematically depicts a non-limiting example of such a probabilistic model. The model receives a first input 401, which are the images captured by the image sensor 114, a second input 405, which is the exhaled breath through the oral cavity and an optional third input 409, which is personal data provided by the wearer of the head-mountable computing device 100. The model further comprises an image processing classification module 403 processing the first input 401 and an oral odour classification module 407 processing the second input 405. Modules 403 and 407 may be implemented by the processor 110, which further implements a logic network 411 such as a Markov logic network to interpret the data provided by modules 403 and 407 and optionally, the user specific data provided via third input 409 to produce an output 413 indicating the most probable diagnosis from the provided inputs, e.g. no halitosis, oral halitosis, systemic halitosis, pseudo-halitosis.

Figure 4:
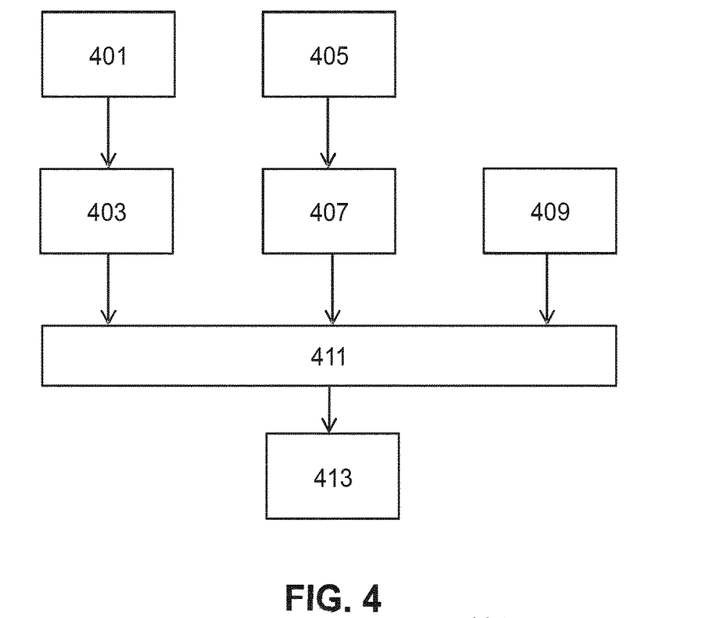
FIG. 4 is a flow chart of an algorithm implemented by a system according to an embodiment.

The model may implement probabilistic reasoning with variables representing:
(1) the image processing classification output and its confidence value;
(2) the e-nose assessment and its confidence values; and
(3) the user data relevant to identify risk factors such as dietary data, smoking data, stress level data, age data, data indicative of oral prostheses being worn (overnight), chronic disease data, historical halitosis diagnostic data generated by the head-wearable computing device 100 or by another device, and so on.

These variables may be intuitively represented using statistical relational approaches such Markov logic for instance. The dependencies between the variables can be flexibly expressed using weighted first order formulae such as:
(0.8) haseNoseOutput(oral_halitosis), i.e. the e-nose module 407 has detected oral halitosis odour with confidence 0.8 (on a confidence scale of 0-1);
(0.6) hasMouthCondition(classB), i.e. the image processing module 405 has classified the mouth condition as unclean but healthy with confidence value 0.6;
(0.9) [hasENoseOutput(oral_halitosis)^¬hasMouthCondition(classB)^hasRiskFactor(chronicalDiseases)⇒hasDiagnosis(oral_halitosis)]; i.e. this rule cites that if the user has an oral_halitosis odour, an unclean but healthy tongue color and no chronical diseases, then oral_halitosis is diagnosed with a confidence value 0.9.

The probabilistic model may be constructed in any suitable manner using any suitable type of formulae using the above parameters as inputs.

In an embodiment, temporal context is added to the model. Particularly, the diagnostic decision making may be based on e-nose data and oral cavity condition data accumulated over a time window with a predefined length. The simplest version integrates the information from the previous time step in order to infer the current one. Following the previous example, such an extension can be easily realized by adding a second argument to the predicates in order to represent different time steps. For example, such formulae may be written as follows:
(0.8) haseNoseOutput(oral_halitosis, t); i.e. at time step t, the e-nose module 407 has detected oral_halitosis odour with confidence 0.8;
(0.6) hasMouthCondition(classB, t); i.e. at time step t, the image processing module 403 has classified the mouth condition as unclean but healthy with confidence value 0.6);
(0.9) [hasENoseOutput(oral_halitosis, t)^¬hasMouthCondition(classB, t)^ hasRiskFactor(chronicalDiseases)⇒hasDiagnosis(oral_halitosis, t)]; i.e. this rule cites that if the user has an oral_halitosis odour, an unclean but healthy tongue color and no chronical diseases at the same time step, then oral_halitosis is diagnosed at that time step with a confidence value 0.9;
(0.9) [hasDiagnosis(oral_halitosis, t−1)⇒hasDiagnosis (oral_halitosis, d)]; i.e. if oral_halitosis is diagnosed is diagnosed at a given time step then that diagnosis will be highly probable at the following time step as well.

This simple temporal reasoning scenario can be flexibly extended to more complex temporal relationships such as by implementing Allen's temporal Algebra as for instance disclosed by Anastasios Skarlatidis et al. in "Probabilistic event calculus based on Markov logic networks", Proceedings of the 5$^{th}$ international conference on Rule-based modeling and computing on the semantic web(RuleML'11), Frank Olken, Monica Palmirani, and Davide Sottara (Eds.). Springer-Verlag, Berlin, Heidelberg, 155-170 (2011). The model parameters, i.e. the formulae weights, may be learned and updated from collecting training data, as is known per se in the art.

The different variable values may be used to generate a maximum a-posteriori inference that determines the most probable state of the unknown variables, i.e. the final diagnosis. Such knowledge engineering formalism may be extended to other functionalities such as the distinction between some specific causes of a diagnosed systemic halitosis. For example, the tongue coating may be classified into finer grained classed as proposed by X. Wang et al. in "An optimized tongue image color correction scheme"; IEEE Transactions on Information Technology in Biomedicine, Vol. 14, no. 6, pp. 1355-1364, 2010. In this manner, systemic diseases such as hypertension can be detected given the corresponding tongue color and the absence of oral malodour.

In the above embodiments, the system for halitosis detection is implemented as a head-mountable computing device 100. Such an implementation facilitates straightforward halitosis detection as the detection may be easily performed while wearing the head-mountable computing device 100 such as smart glasses in front of the bathroom's mirror.

Figure 5:
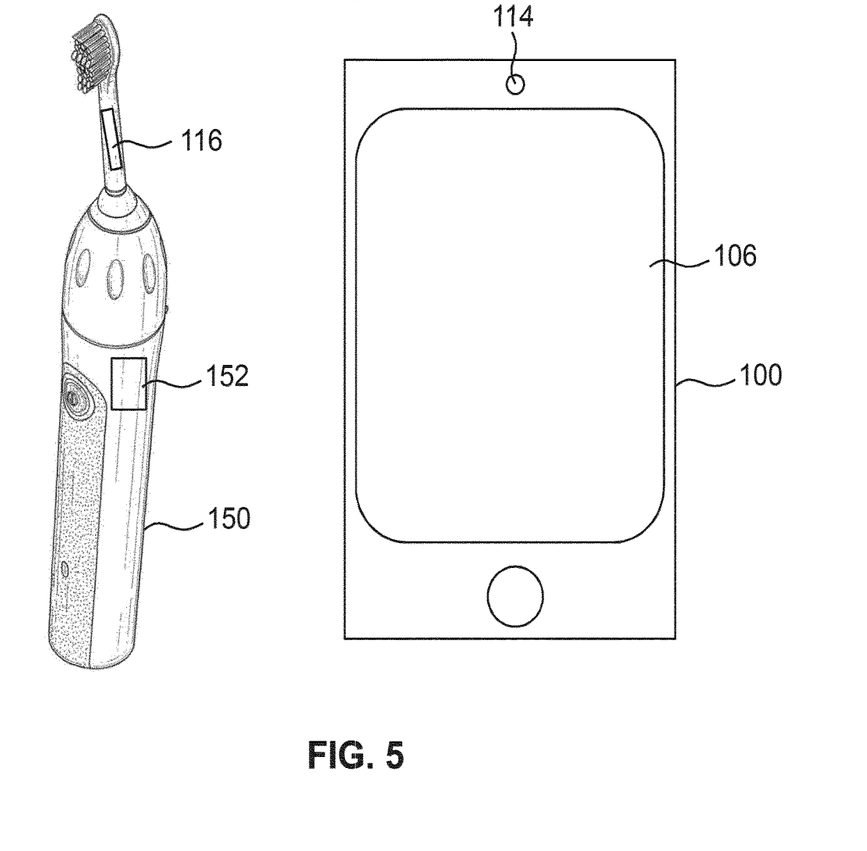
FIG. 5 schematically depicts a system according to an embodiment.

However, in at least some embodiments, the gas sensor 116 may be separate to the head-mountable computing device 100 such that the system for halitosis detection is a modular system. An example embodiment of such a modular system is schematically depicted in FIG. 5, in which the gas sensor 116 is integrated in a device 150 for oral cavity cleaning, i.e. an electronic oral hygiene device 150 such as an electronic toothbrush, an electronic tongue cleaning device, an electronic inter-dental cavity cleaning device, and so on. The device 150 typically comprises a wireless communication module 152 for wirelessly communicating with a wireless communication module of a device 100 comprising the image sensor 114 and optionally comprising one or more display modules 106, e.g. for displaying feedback information, oral cavity cleansing instructions and so on as previously explained. The inclusion of the gas sensor in a device 150 for oral cavity cleaning has the advantage that a particularly sensitive reading of volatile compounds in the exhaled breath that are indicative of halitosis can be generated due to the proximity of the gas sensor 116 to the mouth from which the breath is exhaled.

The device 100 may be a head-mountable computing device although this is not necessary. Alternatively, the device 100 may be a smart mirror or a portable device such as a smartphone or a smart camera.

As previously explained, the use of a head-mountable computing device 100 is particularly advantageous as it facilitates intuitive capture of images from similar angles, position and distance, which is important for consistent image processing of the captured images of the oral cavity. Generally, portable devices and in particular the head-mountable computing device 100 offer the advantage of portability as well as the possibility to integrate the gas sensor 116 within an acceptable range from the mouth, when integrated in the device 100.

Figure 6:
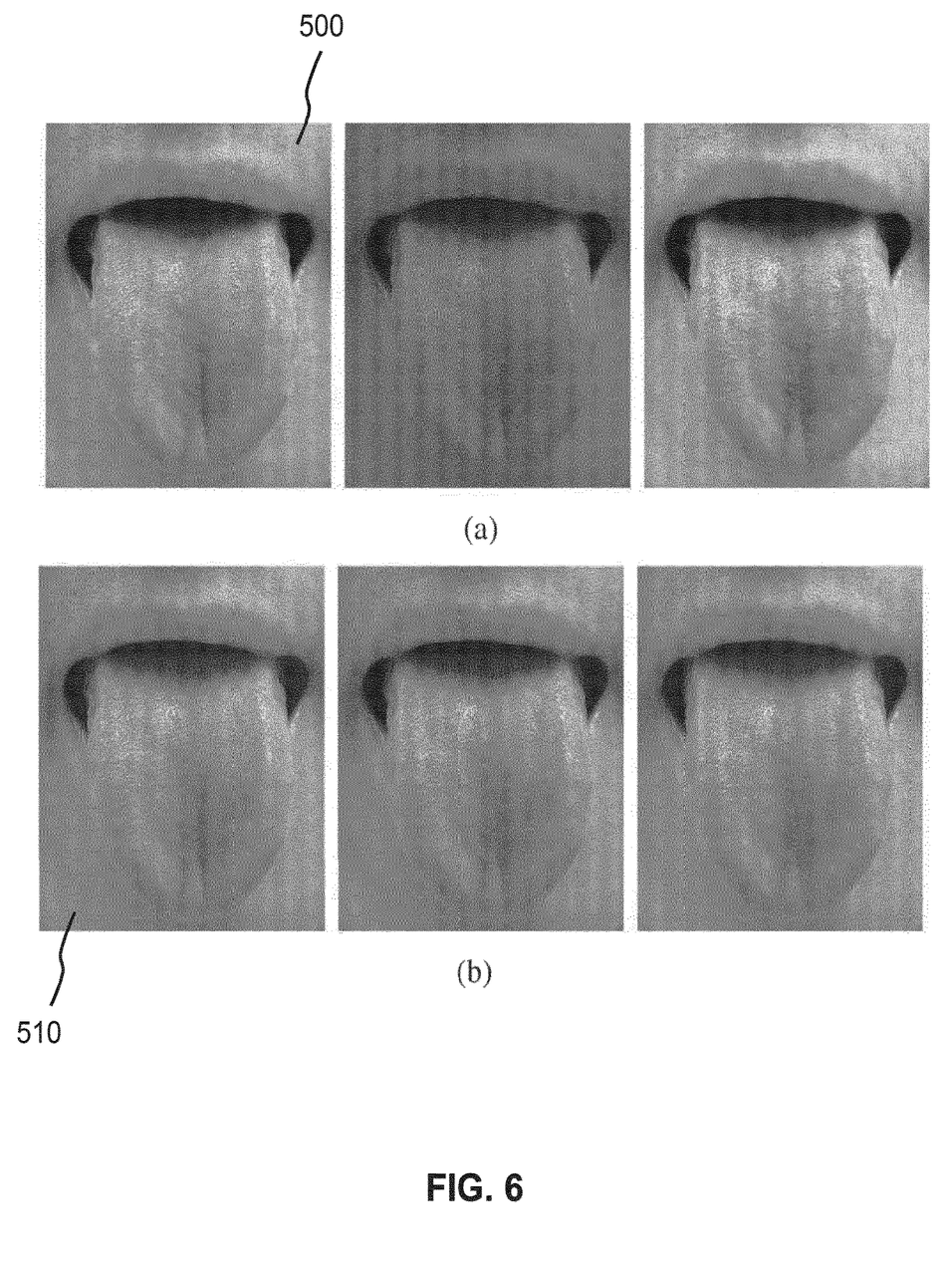
FIG. 6 is a series of tongue images prior to (a) and after (b) image colour normalization as taken by a system according to an embodiment.

In an embodiment, the processor 110 is adapted to apply an image normalization algorithm to the captured image prior to analyzing the image in order to ensure that different images, e.g. images captured by different image sensors 114 when using different cameras to capture the images, e.g. in a modular system for detecting halitosis and/or images captured under different lighting conditions are analyzed in a consistent manner, that is, variations caused by different lighting conditions or colour shades originating from the image capturing conditions are removed from the images prior to their analysis in order to improve the accuracy of the halitosis detection. This is schematically depicted in FIG. 6, in which a series of images 500 marked (a), here of an upper surface of the tongue, clearly exhibit inter-image variations, which variations are removed from the series of images 510 marked (b) by application of a normalization algorithm to the series of images 500 in order to yield the series of images 510. For example, a color correction scheme may be applied that reduces the color difference between images 500 in order to facilitate the extraction of colour feature information from the corrected images 510 as previously explained, e.g. based on the color ratios of the tongue gamut.

Aspects of the present invention may be embodied as a wearable computing device, method or computer program product. Aspects of the present invention may take the form of a computer program product embodied in one or more computer-readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. Such a system, apparatus or device may be accessible over any suitable network connection; for instance, the system, apparatus or device may be accessible over a network for retrieval of the computer readable program code over the network. Such a network may for instance be the Internet, a mobile communications network or the like. More specific examples (a non-exhaustive list) of the computer readable storage medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of the present application, a computer readable storage medium may be any tangible medium that can contain, or store a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out the methods of the present invention by execution on the processor 110 may be written in any combination of one or more programming languages, including an object oriented programming language such as Java, Smalltalk, C++ or the like and conventional procedural programming languages, such as the "C" programming language or similar programming languages. The program code may execute entirely on the processor 110 as a stand-alone software package, e.g. an app, or may be executed partly on the processor 110 and partly on a remote server. In the latter scenario, the remote server may be connected to the wearable computing device 100 through any type of network, including a local area network (LAN) or a wide area network (WAN), or the connection may be made to an external computer, e.g. through the Internet using an Internet Service Provider.

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions to be executed in whole or in part on the processor 110 of the computing device 100, such that the instructions create means for implementing the functions/acts specified in the flowchart and/or block diagram block or blocks. These computer program instructions may also be stored in a computer-readable medium that can direct the computing device 100 to function in a particular manner.

The computer program instructions may be loaded onto the processor 110 to cause a series of operational steps to be performed on the processor 110, to produce a computer-implemented process such that the instructions which execute on the processor 110 provide processes for implementing the functions/acts specified in the flowchart and/or block diagram block or blocks. The computer program product may form part of a computing device 100, e.g. may be installed on the computing device 100.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A system for detecting halitosis, comprising:
 a gas sensor for generating a sensor signal signaling the detection of compounds indicative of halitosis exhaled through an oral cavity;
 an image sensor for capturing an image of a dental condition and/or tongue condition in said oral cavity;
 a processor communicatively coupled to the gas sensor and the image sensor, and adapted to process the sensor signal and the image by applying a probabilistic model to the sensor signal and the image;

wherein applying the probabilistic model includes classifying the sensor signal and the image by using corresponding classification modules and implementing a logic network to interpret data provided by the classification modules to generate an indication of the likelihood of the source of the halitosis; and a display device communicatively coupled to the processor, wherein the processor is adapted to control the display device to display oral hygiene instructions in response to the detection of compounds indicative of halitosis.

2. The system of claim 1, wherein the processor is adapted to generate the indication of the likelihood of the source of the halitosis by interpreting data provided by the classification modules accumulated over a time window with a predefined length.

3. The system of claim 1, wherein the processor is adapted to apply a colour normalization algorithm to the image in order to normalize a tongue or mouth colour prior to processing the image.

4. The system of claim 1, wherein the processor is adapted to determine if, in case of the sensor signal signaling the detection of compounds indicative of halitosis, the halitosis originates from said oral cavity by determining the dental condition and/or tongue condition in the image in combination with evaluating personal data provided by a user of the system.

5. The system of claim 1, wherein:

the gas sensor, the image sensor and the processor are integrated in a single device; or wherein the system comprises a first device including the processor and the image sensor, the first device further comprising a wireless communication module communicatively coupled to the processor and a second device including the gas sensor and a further wireless communication module for communicating with the wireless communication module.

6. The system of claim 5, wherein the system comprises the first device and the second device and wherein the second device is an electronic device for oral cavity cleaning.

7. The system of claim 5, wherein the single device or the first device is a head-mountable device.

8. A method for detecting halitosis, comprising:

receiving a sensor signal from a gas sensor signaling detection of compounds indicative of halitosis exhaled through an oral cavity;

receiving an image of a dental condition and/or tongue condition in said oral cavity from an image sensor;

processing the sensor signal and the image by applying a probabilistic model to the sensor signal and the image;

wherein applying the probabilistic model includes classifying the sensor signal and the image by using corresponding classification modules and implementing a logic network to interpret data provided by the classification modules to generate an indication of the likelihood of the source of the halitosis; and displaying, on a display device, oral hygiene instructions in response to the detection of compounds indicative of halitosis.

9. The method of claim 8, wherein the steps of: receiving a sensor signal signaling detection of compounds indicative of halitosis exhaled through an oral cavity from a gas sensor; receiving an image of a dental condition and/or tongue condition in said oral cavity from an image sensor; and processing the sensor signal and the image; are a) performed prior to cleaning the oral cavity; and
b) repeated after cleaning the oral cavity,
the method further comprising verifying the origin of the halitosis as determined in a) with the origin of the halitosis as determined in b).

10. The method of claim 8, wherein generating the indication of the likelihood of the source of the halitosis is based on interpreting data provided by the classification modules accumulated over a time window with a predefined length.

11. The method of claim 8, further comprising applying a colour normalization algorithm to the image in order to normalize tongue colour prior to processing the image.

12. A non-transitory computer program product comprising a computer-readable data carrier carrying computer program code for, when executed on the system of claim 1, causing the processor of said system to implement the method of claim 8.

* * * * *